United States Patent [19]

Woo et al.

[11] 4,403,606
[45] Sep. 13, 1983

[54] COMPATIBLE INTERNAL BONE FIXATION PLATE

[75] Inventors: Savio L-Y. Woo, Encinitas; Wayne H. Akeson, La Jolla, both of Calif.

[73] Assignee: The Regents of the University of California, Berkeley, Calif.

[21] Appl. No.: 148,204

[22] Filed: May 9, 1980

[51] Int. Cl.³ .......................... A61F 5/04; A61B 17/18
[52] U.S. Cl. ...................................... 128/92 D; 3/1.9; 128/92 G
[58] Field of Search ................ 128/92 D, 92 G, 92 R, 128/92 BC, 92 C; 3/1.9, 1.91

[56] References Cited

U.S. PATENT DOCUMENTS

| | | | |
|---|---|---|---|
| 2,406,832 | 9/1946 | Hardinge | 128/92 D |
| 2,486,303 | 10/1949 | Longfellow | 128/92 D |
| 3,893,196 | 7/1975 | Hochman | 128/92 BC X |
| 4,040,129 | 8/1977 | Steinemann et al. | 128/92 D X |
| 4,089,071 | 5/1978 | Kalnberz et al. | 128/92 C X |
| 4,219,015 | 8/1980 | Steinemann | 128/92 D |
| 4,297,993 | 11/1981 | Harle | 128/92 D |

FOREIGN PATENT DOCUMENTS

| | | | |
|---|---|---|---|
| 2213283 | 8/1973 | Fed. Rep. of Germany | 128/92 D |
| 2603456 | 8/1977 | Fed. Rep. of Germany | 3/1.9 |
| 400317 | 2/1974 | U.S.S.R. | 128/92 G |

OTHER PUBLICATIONS

Implants in Surgery (Book) by D. F. Williams et al., W. B. Saunders Co. Ltd. (Publisher), London, Philadelphia, Toronto, 1973, pp. 89–94.
"A Simple Method of Onlay Bone Grafting", by A. Young et al., The Lancet, Dec. 8, 1962, pp. 1186–1187.
"Potential Application of Graphite Fiber and Methyl Methacrylate Resin Composites as Internal Fixation Plates", by S. L-Y. Woo et al., J. Biomed. Mater. Res., vol. 8, No. 5, Sep. 1974, pp. 321–338.

Primary Examiner—Ronald L. Frinks
Attorney, Agent, or Firm—Poms, Smith, Lande & Rose

[57] ABSTRACT

An internal fixation plate for bridging two portions of a broken bone is formed to have properties, in terms of bending, axial, and torsional stiffness suitable for the bone being mended. These properties include high resistance to bending and torsional stresses, and relatively low axial stiffness. One plate configuration which has been determined to have the desired stiffness properties is an elongated flat hollow metal plate or tube. Arrangements are provided for precluding bone ingrowth, and this may be achieved by filling the member with a medically inert substance, such as silicone rubber or ultra high molecular weight polyethylene, or by sealing the openings into the tubular plate. The materials of the bone fixation plate may be selected for their mechanical properties, and also as biologically inert substances which will not have adverse physiological effects when embedded in the human body.

8 Claims, 14 Drawing Figures

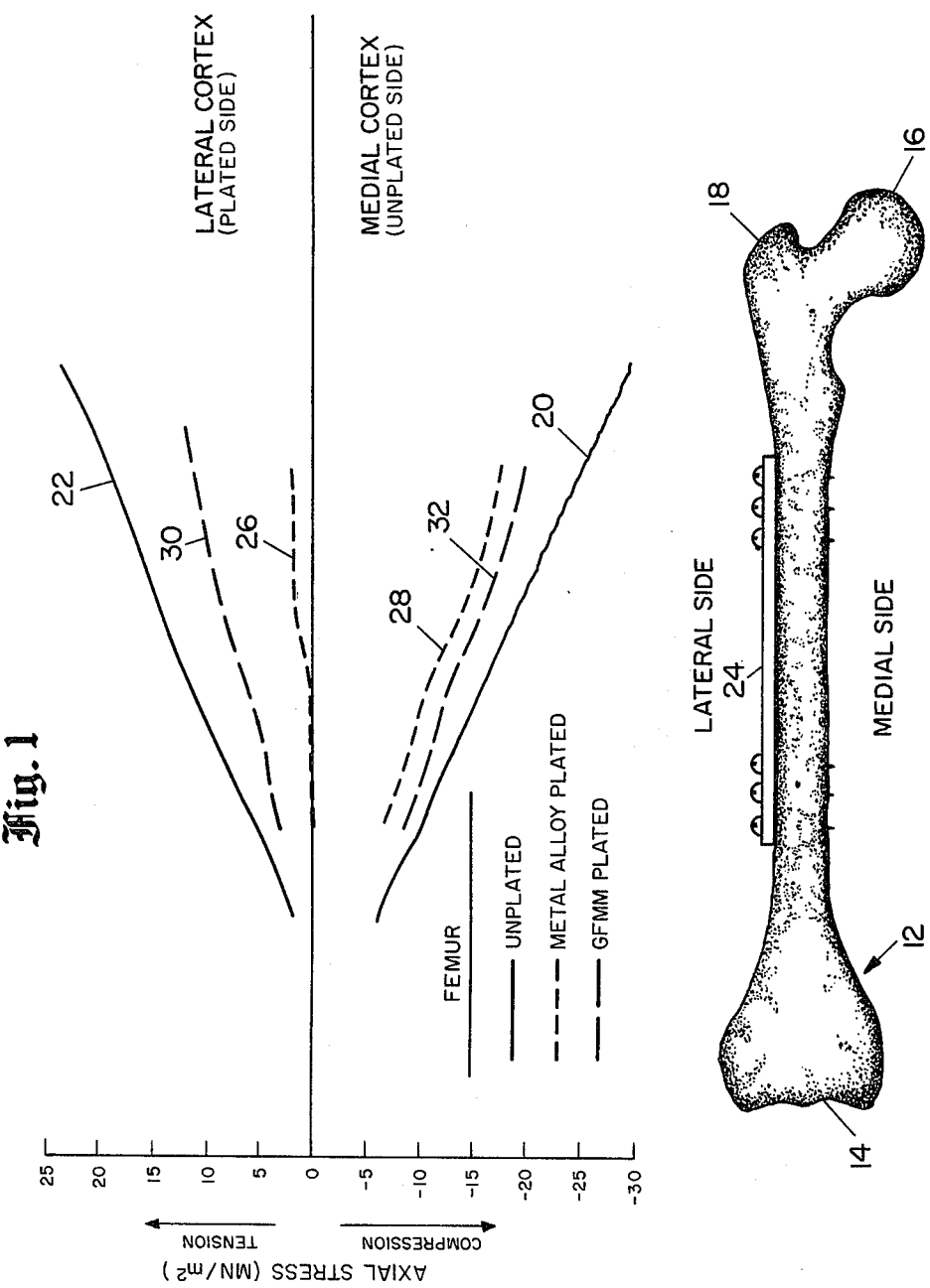

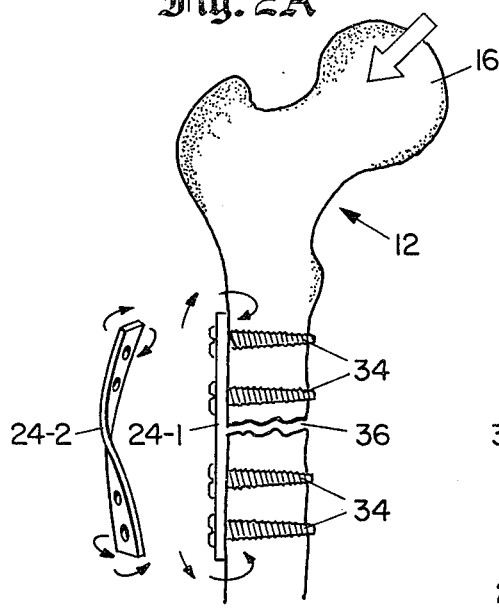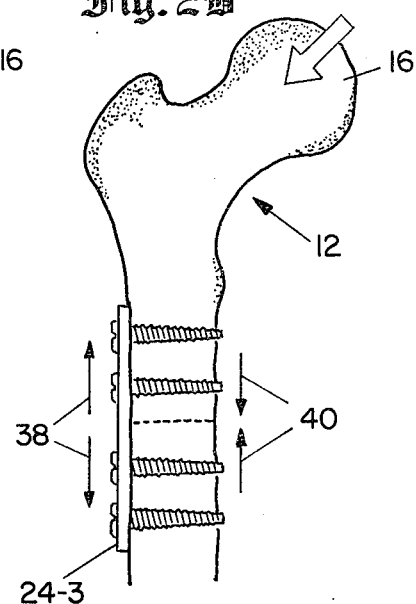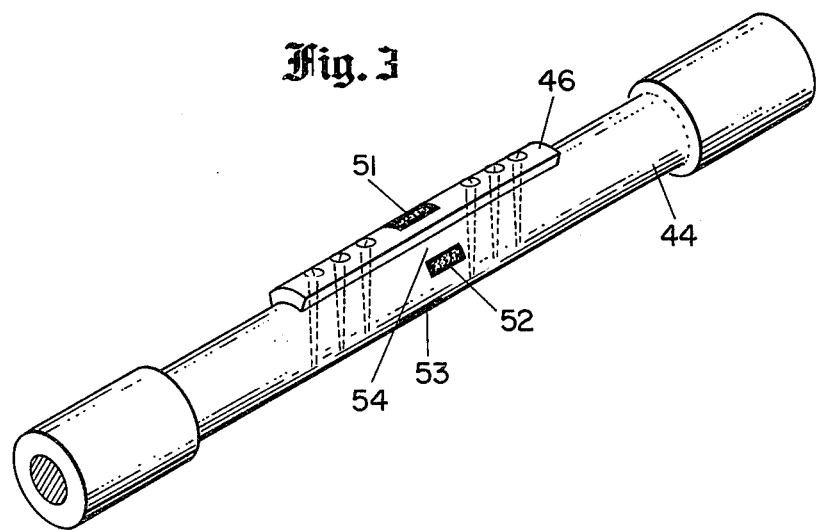

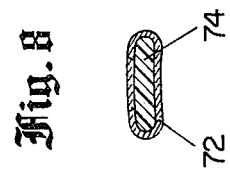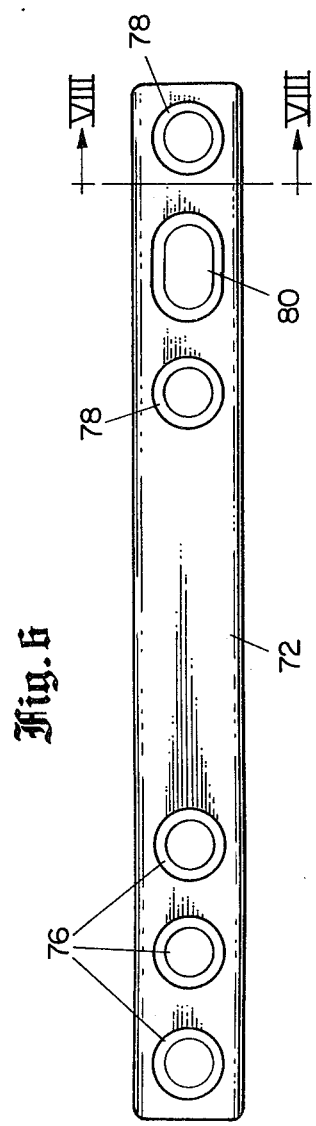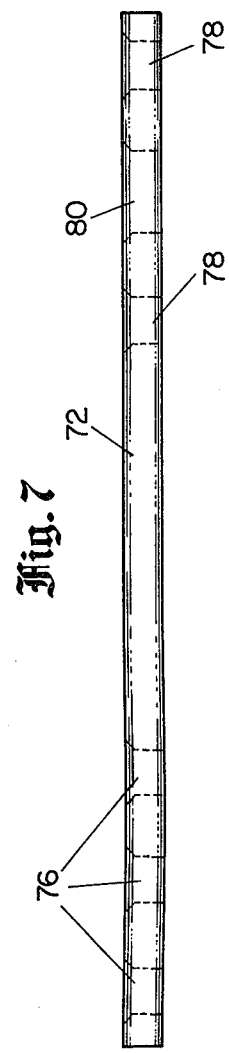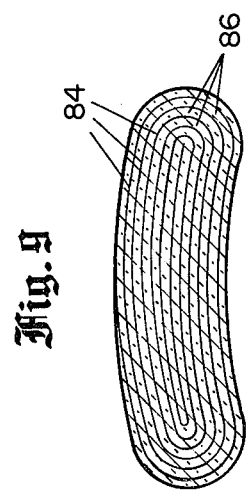

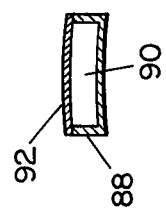
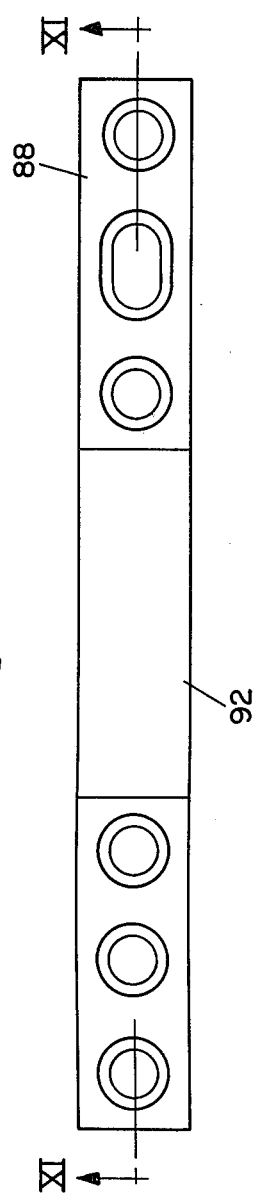
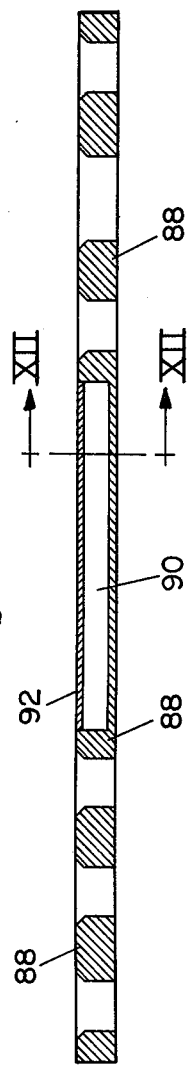
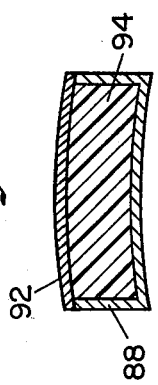

COMPATIBLE INTERNAL BONE FIXATION PLATE

The invention described herein was made in the course of or under a grant from the National Institute of Health.

BACKGROUND OF THE INVENTION

This invention relates to internal bone fixation plates.

Clinical experience has established quite clearly that under appropriate conditions, the internal fixation of fractures of long bones of the human body (diaphyseal fractures) with sturdy metal plates is effective in the achievement of fracture healing. However, an undesirable consequence of the rigidity of the internal fixation plates which have been generally used up to the present time is the localized weakening or reduction in strength of the bone which accompanies the protection of the underlying bone from normal stresses after the fracture has been healed. This phenomenon of abnormal rarefaction of the bone is referred to by the medical term "osteoporosis." Following removal of the plate, the weakened bone is vulnerable to refracture and remains so for several weeks or even months, particularly in cases where two plates have been employed. Incidentally, the phrases "plating" and "plated" will frequently be employed in the present specification to refer to bones to which internal fixation plates have been applied.

In the last two decades, the overriding emphasis has been on the development of greater strength of such fixation plates through the provision of heavier plates, and the evolution of concepts such as compression plating. This approach has met with considerable success. However, up to the recent past, this approach has clearly not achieved optimum results, as the long term adverse physiological response of bone to such sturdy devices has been largely ignored.

In recent years, however, considerable interest has been generated in the possible use of less rigid internal fixation plates for fracture management, in view of the fact that the very sturdy compression plates overprotect the underlying healed fracture. In addition to a weakening of the cortex or outer wall the bone, a loss of substance of the periosteum has been noted in tests with dog femurs. Incidentally, the term "periosteum" refers to a specialized connective tissue covering all bones and possessing bone-forming potentialities or capabilities. In addition, incomplete mineralization at the cortex beneath the sturdy metal plate was observed, and bone remodeling and improved strength and increased substance of the bone (including regression of osteopenia, to use medical terminology), started soon after removal of the rigid plate.

Reference is now made to an article entitled, "Potential Application of Graphite and Methyl Methacrylate Resin Composites as Internal Fixation Plates," By S. L-Y. Woo and W. H. Akeson, B. Levenetz, R. D. Coutts, J. V. Matthews, and D. Amiel, Journal of Biomedical Materials Research, Vol. 8, No. 5, September 1974, Pages 321 to 338. In that paper we described a graphite fiber methyl methacrylate composite (GFMM) material which was employed to form softer plates used in the study of fracture healing in dog radii. Traditional sturdy stainless steel plates with tenfold higher axial and flexural stiffness were used as controls. Using combined biomechanical testing and morphometric methods, we noted that at four months postplating, the torsional strength of the whole radius was similar for the composite and the metal plated sides. Morphometric studies using tetracycline labelling techniques showed significantly higher cortical porosity on the metal plated side (14%) as compared to the GFMM plated side (6.3%).

However, the mere selection of softer or less rigid materials to avoid long term adverse effects runs counter to the basic immediate problem of firmly setting the broken bones in their desired relative position. Obviously, if the internal fixation plate is too soft or flexible, a single plate will not hold the bones sufficiently firmly to permit prompt fracture healing.

Accordingly, a principal object of the present invention is to provide an internal bone fixation plate which is not only sufficiently rigid to provide immobilization in the early stages of fracture healing, but is not so rigid as to cause bone deterioration following the initial healing stage.

SUMMARY OF THE INVENTION

In accordance with the present invention, it has been determined that it is primarily resistance to bending and torsion which is needed during the initial stages of fracture healing, and it is relatively low resistance to axial stress which is required during the later stages of healing to avoid osteoporosis and the other adverse effects which occur when the normal axial stress is not received by the bone.

Further, it has been determined that bone fixation plates having the desirable mechanical features and which are compatible with bone strength are achieved when the fixation plate is formed in a manner similar to the structure of a bone, with a rigid outer shell and a hollow or nonstructural central core.

In one embodiment, a fixation plate having the desired mechanical characteristics is formed of a hollow plate which has a tubular cross-section, and which is also curved somewhat to fit the outside curvature of normal long human bones, such as those of the arm or the leg. In addition, openings into the center of the fixation plate are blocked from bone of soft tissue ingrowth, either by closing these openings or by filling the central portion of the hollow fixation plate with a polymeric material, such as ultra high molecular weight polyethylene or silicone which are medically inert. In addition, suitable holes are provided through the elongated fixation plate to secure it to the two portions of the bone which are being set.

From a broad aspect, it is contemplated that an elongated internal bone fixation plate, provided with conventional openings at either end for securing to the two parts of a broken bone, is formed to have relatively high resistance to bending and torsion, but relatively low axial stiffness, thereby providing both the initial strength for early healing of the bone, and the subsequent low axial stiffness needed to inhibit weakening of the bone through over protection.

Although the hollow tubular configuration outlined hereinabove is preferred, the desired structural properties of high torsional stiffness and resistance to bending, and relatively low axial stiffness may be achieved in other ways. For example, carbon filament sheet material may be impregnated with surgical epoxy, methyl methacrylate cement, or other biocompatible polymeric cementing material, and rolled up; and the resultant elongated roll may be flattened and molded to the configuration of a conventional internal bone fixation plate. By selecting suitable carbon filament thicknesses, proper orientation of the filaments forming the sheet material, the density of the sheet material, as well as the nature of the cementing material, the desired anisotropic mechanical properties may be obtained.

In the preferred embodiments, the fixation plates are about the same in their external dimensions to the sturdy solid metal plates which have been employed, and are hollow structural members of biologically inert metal, such as stainless steel or of the known metals employed in conventional solid metallic plates. The wall thickness of the active hollow portion bridging the bone fracture, is preferably less than ten percent of the maximum transverse dimension of the fixation plate. For example, a wall thickness for stainless steel of about 0.028 inch may be employed with a plate which has an overall width of about 0.375 inch and a thickness of about 0.153 inch. Under these conditions bending and torsional stiffness is more than two-thirds that of a rigid plate (i.e. solid plate of same width and thickness), and axial stiffness is less than one-third that of such a plate. With somewhat greater wall thickness, such as one-fifth of the maximum transverse dimension, a significant reduction in axial stiffness would be achieved, with some reduction in osteoporosis, as compared with a solid plate, but the thinner wall thickness is preferred. With metals of different mechanical properties, it is to be expected that some departures from the figures set forth herein will be appropriate.

It is also noted that, as compared with fixation plates of U-shaped or other similar non-tubular cross-sectional configuration, the tubular or hollow fixation plates will have greatly increased torsional stiffness, in the order of ten times or more that of the U-shaped fixation plates. Typical prior U-shaped or non-closed cross-sectional configuration fixation plates are shown in U.S. Pat. Nos. 2,406,832, granted Sept. 3, 1946 to M. G. Hardinge; and 4,040,129, granted Aug. 9, 1977 to S. G. Steineman et al.

Other objects, features, and advantages of the present invention will become apparent from a consideration of the following detailed description and from the accompanying drawings.

BRIEF DESCRIPTION OF THE DRAWINGS

FIG. 1 is a diagram indicating the axial tension and compression stresses of an intact upper leg bone or femur;

FIG. 2A and FIG. 2B illustrate the differences in loads on internal fixation plates during early fracture healing, and later bone remodeling, respectively;

FIG. 3 illustrates an experimental model of a plated magnesium tube simulating the stresses in a long bone, such as the femur;

FIGS. 6 and 7 are top and side views, respectively, of the fixation plate of FIG. 5;

FIG. 8 is a cross-sectional view taken along lines VIII—VIII of FIG. 6;

FIG. 9 is a cross-sectional view through an alternative embodiment of the invention;

FIGS. 10, 11 and 12 are three views of an alternative hollow fixation plate; and FIG. 13 shows a modified form of the fixation plate of FIGS. 10 through 12.

DETAILED DESCRIPTION

Figure 4:
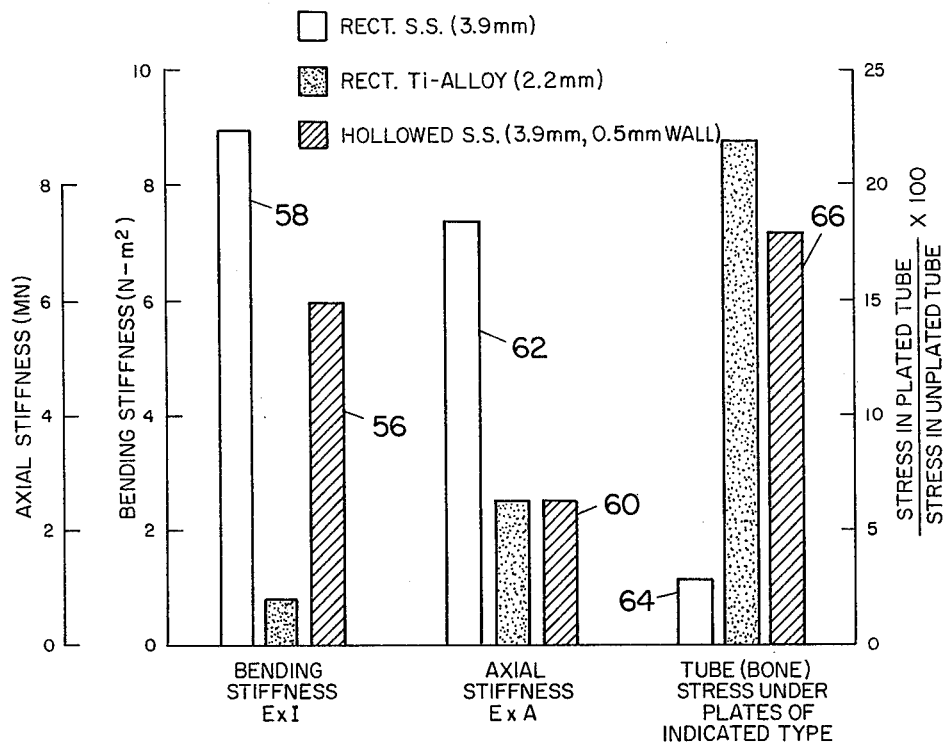
FIG. 4 is a comparison of bending and axial stiffness of three different internal fixation plate designs.

Referring more particularly to the drawings, FIG. 1 shows a femur 12 with the end 14 forming part of the knee joint shown to the left, and the substantially spherical end 16 which forms part of the hip joint appearing to the right in FIG. 1. The protruberance 18 is medically known as the "greater trochanter," to which several muscles are attached.

In medical terminology, the "medial" side is toward the center of the body, and the "lateral" side is toward the outside of the body. In FIG. 1, the medial side of the femur is shown toward the bottom of the figure, and the lateral side is toward the top of the figure. This is readily confirmed by the fact that the ball 16 which extends inward toward the hip joint from the main portion of the leg extends downward in the showing of FIG. 1. The graphs in FIG. 1 shown by the solid lines 20 and 22, represent the axial stress in the cortex, or outer wall of the femur along the length of the medial side (Reference numeral 20) which is under compression, and along the lateral side (Reference numeral 22), which is under tension. It is noted that the internal fixation plate 24 is affixed to the lateral side of the femur (normally under tension). When a single plate is used, it is obviously much better from a stress standpoint to have the plate located on the side of the femur which is under tension, rather than that which is under compression, and which will therefore remain pressed together under normal stress conditions.

The normal heavy internal fixation plates are often made of special alloys such as "Zimalloy" or "Vitallium." The test of FIG. 1 used a Vitallium fixation plate. With the plate in place, the plot 26 indicates very little stress in the lateral cortex, as all of the stress is being absorbed by the plate. However, on the medial side, the plot 28 indicates only a modest departure from the normal unplated characteristic 20. The soft or more flexible GFMM plates produce the characteristics 30 and 32 which are moderate departures from the other two characteristics and are intermediate the previously discussed plots. As mentioned above, the problem with the GFMM softer and more flexible plate is that a single plate does not tend to provide enough rigidity and strength against bending and torsional movement to adequately insure initial setting and healing of the bone.

Referring now to FIGS. 2A and 2B, FIG. 2A indicates diagrammatically the forces which are present during initial fracture healing; and FIG. 2B shows the forces present during bone remodeling. In FIG. 2A, the internal fixation plate 24-1 has been secured by the screws 34 to the femur 12 on both sides of the break 36. The break 36 is shown somewhat enlarged and will normally be set with the two matching portions in close engagement with one another. In all events, during the initial fracture healing phase, the plate 24-1 will be subject to significant bending and torsion stresses, as indicated by the arrows which appear in FIG. 2A and by the exaggerated configuration of the showing of the plate 24-2 immediately adjacent the plate 24-1.

FIG. 2B shows the bone remodeling phase, during the time period following the initial week or so when fracture healing occurs. As indicated by the arrows 38 and as discussed hereinabove, during this stage the plate 24-3 is in tension, and the opposite, medial, side of the femur is in compression, as indicated by the arrows 40.

As mentioned hereinabove, during the bone remodeling stage as shown in FIG. 2B, the very high strength and sturdy nature of the solid metallic fixation plates which are generally used has caused a weakening and a porosity in the cortex of the bone, particularly on the lateral side of the femur and underlying the fixation plate which is carrying substantially all of the load.

It may be seen from FIGS. 2A and 2B, that the strength required of the fixation plate during the fracture healing stage is resistance to bending and torsion; while during the bone remodeling stage, a relatively low axial stiffness would be desirable to prevent atrophying, osteoporosis, or osteopenia of the lateral cortex of the bone. The present invention involves the development of fixation plates having the desired high resistance to bending and torsion, but relatively low axial stiffness.

FIG. 3 shows a magnesium tube 44 which was employed to simulate a long bone, with the cortex of the bone being simulated by the hollow shell of the magnesium tube 44. A fixation plate 46 was secured to the tube as shown in FIG. 3, and stress was measured directly by the strain gauges 51, 52 and 53. The stress at point 54 directly beneath the fixation plate within the wall of the magnesium tube could not be measured experimentally, and therefore was calculated.

FIG. 4 shows the results of tests using the arrangement of FIG. 3, with three different types of fixation plates. The bar graphs are identified in the legend associated with FIG. 4 and the open bar graphs represent results obtained with a solid rectangular stainless steel fixation plate 3.9 millimeters in thickness. The stippled bar graphs represent a softer titanium alloy of solid material which was 2.2 millimeters thick. This softer and more flexible fixation plate, in which some interest has recently been shown, is principally formed of titanium, with 6 percent aluminum and 4 percent vanadium. The bar graphs shown provided with sectioning lines represent the results of hollow stainless steel fixation plates having a total thickness of 3.9 millimeters, the same as the solid rectangular stainless steel elements, but the wall thickness of the stainless steel outer shell was only ½ of a millimeter.

Focusing on the differences between the open bar graph showings and those which are cross-sectioned, it may be seen that the bending stiffness represented by the bar 56 is very nearly es great as that of the solid stainless steel fixation plate as represented by the bar graph 58. On the other hand, the axial stiffness for the new hollow type of fixation plate as shown by the bar 60 is in the order of one third of the solid stainless steel plate represented by the bar graph 62. Similarly, the stress which would occur during bone remodeling is very low for the solid stainless steel plate, as indicated by the bar graph 64, while it is relatively high for the hollow element, as represented by the bar graph 66. This relatively high axial stress during bone remodeling means that osteoporosis and the other adverse effects mentioned hereinabove, will be minimized.

The stippled bars in FIG. 4 are typical of the softer or less stiff isotropic bone fixation elements which have been proposed during the last five or ten years. They permit relatively high axial stress during bone remodeling, but do not provide adequate bending or torsional stiffness during the fracture healing phase to be satisfactory.

Incidentally, in connection with the showings of FIG. 4, the torsional stiffness generally follows the bending stiffness for the fixation plates under consideration, and therefore has not been shown separately.

Figure 5:
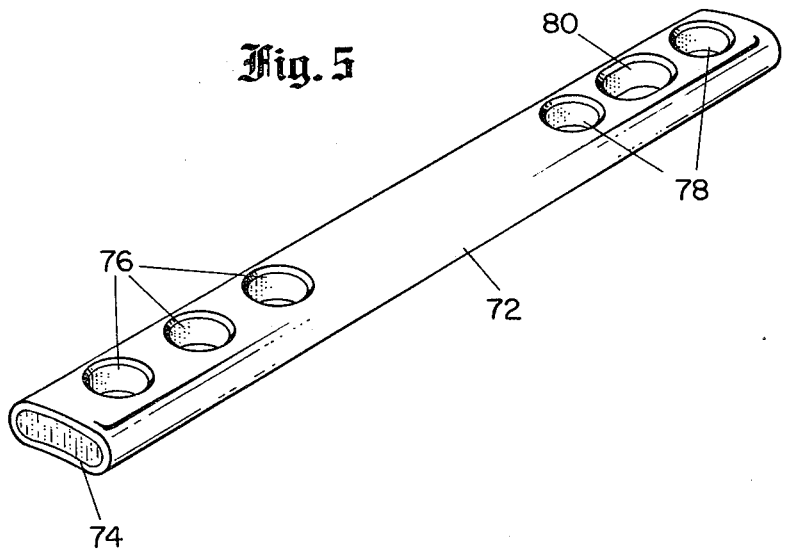
FIG. 5 is an isometric view of an internal fixation plate having a metallic outer shell and a polymeric filler.

FIG. 5 is an isometric view, and FIGS. 6, 7 and are conventional top, side, and cross-sectional views of a fixation plate in accordance with the present invention. As shown in FIG. 5, the fixation plate includes a continuous outer tubular body 72 and filler material 74, which may be ultra high density polyethylens, located within the tubular shell to prevent bone ingrowth. The outer tubular shell may be made of any of a number of known biologically inert metallic alloys, such as the cobalt, chromium, molybdenum alloys known under the trademark "ZIMALLOY," for example. The high density polyethylene is also biologically inert, and has good mechanical strength for supporting the screws, while also having relatively low compressional stiffness.

In accordance with the conventional techniques, the fixation plate includes three standard circular holes 76 at one end, and two standard size holes 78 at the other end, with one elongated hole or opening 80 intermediate the two circular holes 78 at the second end. As best shown in FIG. 6, the central hole 80 is employed in the course of pulling the two parts of the fractured bone more closely together. More specifically, the fixation plate is initially secured to one portion of the broken bone by three screws through the holes 76. Then one screw is fastened through the outer portion of the hole 80 furtherest away from the holes 76 and is left slightly loose without full tightened engagement with the rim of the fixation plate. Pressure is then brought to bear on the screw extending through the outer portion of the hole 80, relative to the fixation plate 72, and the mating surfaces of the bone, where it has been broken, are brought closer together. Then the two additional screws are fastened into the bone through the outer holes 78, and the third screw through the opening 80 is further tightened. This completes the mechanical securing of the fixation plate to the two portions of the broken bone.

Other structural features which may be noted include the counter sinking of the holes, so that the screwheads do not extend significantly above the surface of the plate, as such protrusion could interfere with the movement of muscles or other tissues past the fixation plate. Also, as best shown in FIG. 8, the plate may be slightly curved to better fit the rounded outer surface of the bones to which it is to be secured.

Incidentally, in the course of the manufacture of the fixation plate as shown in FIGS. 5 through 8, an initial circular thin-walled tube is reformed through the use of successive mandrels to the shape indicated in FIG. 8. High density polyethylene material is then molded into the center of the tube. After it has hardened, the holes and counter sinking machining operations are accomplished.

The fixation plates are made in a number of standard sizes. One unit suitable for use with the bones of the forearm, the radius or the ulna, could be 3.55 inches in length, 0.153 inches in thickness, and 0.375 inches in lateral extent. The wall thickness of the metal tubing could be in the order of 0.28 inches. The spacing between the holes 76 may be in the order of 0.375 inches. The holes may be 7/64th inch countersunk holes formed to match the head configuration of Woodruff type screws. The outer holes 76 and 78 may be located in the order of 0.175 inch from the end of the fixation plate. The corners may be provided with a slight radius and the tubes should be deburred and carefully polished to avoid any rough edges which might be abrasive to tissue.

In the foregoing paragraph, typical dimensions for a fixation plate applicable to fractures of the forearm were given. It is to be understood that fixation plates are formed in many sizes and configurations to suit the needs of orthopedic surgeons for various types of broken bones. Accordingly, the dimensions set forth hereinabove are merely representative and are not to be considered as limiting.

FIG. 9 is a cross-sectional showing of an alternative fixation plate in accordance with the invention in which a composite plate formed of a rolled-up sheet of carbon filament fibers 89 and a suitable cementing material such as methyl methacrylate 86, is employed. More specifically, a sheet of carbon filament fibers is formed by laying out two layers of the fibers on a flat surface, with the two layers at a suitable angle relative to one another, and applying a suitable cement such as methacrylate to them by spraying or the like. The cement impregnated fiber sheet material is then rolled up tightly to form a spiral roll. The resultant roll is then placed in a mold having an inner surface configuration corresponding to the outer cross-sectional configuration as shown in FIGS. 8 or 9. Subsequently, after the composite fixation plate has hardened, it is subject to machining operations to provide the holes as indicated in FIG. 6, for example, and the outer surface of the composite fixation plate is smoothed by appropriate sanding, grinding or other similar operations, to provide a smooth exterior surface. The resultant plate has similar anisotropic properties to the tubular unit of FIGS. 5 through 8, in that it has high resistance to bending and torsional stress, but low axial stiffness.

Another alternative bone fixation plate is shown in FIGS. 10 through 12. The overall external configuration of the plate of FIGS. 10 through 12 is similar to that of the fixation plate of FIGS. 5 through 8. It is formed from a conventional solid stainless steel or other biologically inert metal plate 88, having an opening 90 milled into its central portion. A plate 92 of the same material is welded over the opening 90 to form the central tubular active portion of the fixation plate, which will bridge the bone fracture. FIG. 11 is a central cross-sectional view taken along lines XI—XI of FIG. 10; and FIG. 12 is a cross-sectional view taken along line XII—XII of FIG. 11, through the central hollow or tubular portion of the plate. FIG. 13 is a cross-sectional showing of an alternative embodiment in which the hollow space is filled with material 94 having low resistance to longitudinal stress, and which will preclude bone or tissue ingrowth in the event the welding of the plate 92 into place is not 100 percent perfect and has left a few small openings. The material 94 may be ultra high density polyethylene silicone rubber or other polymeric material. Incidentally, the dimensions and the wall thickness of the hollow portion (0.028 inch) may be substantially the same for the embodiments of FIGS. 10 through 13 as for that of FIGS. 5 through 8. Accordingly, bone or tissue ingrowth may be precluded when hollow metallic fixation plates are employed, either by sealing the opening or openings into the plate or by the presence of biologically inert material of low mechanical stiffness within the hollow fixation plate.

In conclusion, it is to be understood that the foregoing detailed description and the accompanying drawings merely describe specific embodiments of the invention. Other specific dimensions and materials may be employed to achieve the same results. For example, instead of filling the tubular fixation plate with ultra high molecular weight polyethylene, other materials having relatively low mechanical stiffness and which are biologically inert may be employed. Accordingly, the present invention is not limited to that precisely as shown in the drawings and as described hereinabove.

What is claimed is:

1. A compatible internal fixation plate for diaphyseal bone fractures comprising:
   a hollow elongated flat metal plate formed of biologically inert material;
   said plate being provided with a plurality of transverse openings at each end for securing the plate to the bone on both sides of the fracture;
   said plate including means for providing high bending and torsional stiffness but relatively low axial stiffness relative to a conventional solid metal fixation plate, said means including a continuous outer metallic surface with opposed inner walls spaced apart from one another to form a hollow metal-free central zone;
   means for precluding bone ingrowth into the metal-free central zone of said plate; and
   said plate including continuous integral structural metallic means extending between said openings at each end of said plate;
   whereby bending and torsional rigidity is provided for early fracture healing, and the low axial stiffness of the plate inhibits osteoporosis and bone weakening during later stages of bone remodeling before the plate is removed.

2. A compatible internal fixation plate as defined in claim 1 wherein the wall thickness of each of the walls of said hollow fixation plate is less than one-tenth of the maximum transverse dimension of said fixation plate.

3. A compatible internal fixation plate as defined in claim 1 wherein the wall thickness of each of the walls of said hollow fixation plate is less than one-fifth of the maximum transverse dimension of said fixation plate.

4. A compatible internal fixation plate as defined in claim 1 wherein at least one surface of said plate is curved in a plane transverse to the longitudinal axis of said plate for closer engagement with the outer surface of the bone to which it is to be secured.

5. A compatible internal fixation plate as defined in claim 1 wherein said metal plate is hollow only in the central zone between said transverse openings.

6. A compatible internal fixation plate for diaphyseal bone fractures comprising:
   a hollow elongated flat metal plate formed of biologically inert material;
   said plate being provided with a plurality of transverse openings at each end for securing the plate to the bone on both sides of the fracture;
   said plate having a continuous outer metallic surface with opposed inner walls spaced apart from one another to form a hollow metal-free central zone, and provide high bending and torsional stiffness, but relatively low axial stiffness relative to a conventional solid metal fixation plate; and
   means for precluding bone ingrowth into the metal-free central zone of said plate; said means comprising biologically inert polymeric material having relatively low stiffness substantially filling the central hollow zone of said plate;
   whereby bending and torsional rigidity is provided for early fracture healing, and the low axial stiffness of the plate inhibits osteoporosis and bone weakening during later stages of bone remodeling before the plate is removed.

7. A compatible internal bone fixation plate as defined in claim 6 wherein said biologically inert plastic material is high density polyethylene.

8. A compatible internal fixation as defined in claim 6, wherein said polymeric material is ultra high molecular weight polyethylene.

* * * * *